US006773430B2

(12) United States Patent
Hofer

(10) Patent No.: US 6,773,430 B2
(45) **Date of Patent: *Aug. 10, 2004**

(54) MOTION DETECTOR FOR EYE ABLATIVE LASER DELIVERY SYSTEMS

(75) Inventor: Richard A. Hofer, Santa Cruz, CA (US)

(73) Assignee: Visx, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/370,457

(22) Filed: Aug. 9, 1999

(65) Prior Publication Data

US 2002/0077622 A1 Jun. 20, 2002

(51) Int. Cl.[7] .................... A61F 9/007

(52) U.S. Cl. .................... 606/12; 606/5; 606/10; 606/13

(58) Field of Search .................... 606/2, 3–13, 17

(56) References Cited

U.S. PATENT DOCUMENTS 3,723,013 A 3/1973 Stirland et al.
4,665,913 A * 5/1987 L'Esperance, Jr. ............. 606/3
4,911,711 A * 3/1990 Telfair et al. .................. 606/5
4,973,330 A 11/1990 Azema et al.
5,383,026 A 1/1995 Mouri et al.
5,399,870 A 3/1995 Torii et al.
5,401,979 A 3/1995 Kooijman et al.
5,450,143 A 9/1995 Rowe et al.
5,490,849 A 2/1996 Smith
5,548,354 A 8/1996 Kasahara et al.
5,549,599 A 8/1996 Sumiya
5,633,716 A 5/1997 Corby, Jr.
5,657,128 A 8/1997 Muller et al.
5,689,331 A 11/1997 Staver
5,770,850 A 6/1998 Bowen et al.
5,772,656 A 6/1998 Klopotek
5,827,264 A 10/1998 Hohla
5,928,221 A 7/1999 Sasnett et al.
6,022,108 A 2/2000 Yoshida et al. ............. 351/208
6,027,216 A 2/2000 Guyton et al. .............. 351/200
6,027,494 A 2/2000 Frey .............................. 606/5
6,030,376 A 2/2000 Arishima et al. .............. 606/4
6,210,169 B1 4/2001 Yavitz
6,210,401 B1 4/2001 Lai

FOREIGN PATENT DOCUMENTS

EP 0280414 A1 8/1988

* cited by examiner

*Primary Examiner*—David M. Shay
(74) *Attorney, Agent, or Firm*—Townsend and Townsend and Crew LLP; Lynn M. Thompson

(57) ABSTRACT

Improved systems, devices, and methods are provided for verifying the scanning motion or adjustment of a laser beam. The system can advantageously be used in laser eye surgery where accurate control of the laser beam is crucial for patient safety and successful vision correction. In one embodiment, a laser system is provided for sculpting a portion of the eye. The system includes a laser for generating a laser beam suitable for ablation of a portion of the eye. A laser beam adjustment mechanism is optically coupled to the laser beam from the laser. The adjustment mechanism scans or adjusts the laser beam in accordance with a predetermined ablation pattern of the laser beam on the eye. An energy motion sensor optically coupled to the laser beam downstream from the adjustment mechanism is provided to verify adjustment of the laser beam in accordance with the ablation pattern. Typically, the energy motion sensor has a mask arranged to block varying portions of the laser beam in response to laser beam adjustment. Positioning of the laser beam is verified by comparing anticipated energy readings from the sensor based on the expected positional adjustment of the beam on the mask and actual energy readings measured by the sensor during the eye ablative procedure.

32 Claims, 4 Drawing Sheets

272
y - axis
240
250
270
x - axis
252
260
262

MOTION DETECTOR FOR EYE ABLATIVE LASER DELIVERY SYSTEMS

BACKGROUND OF THE INVENTION

The present invention relates generally to medical systems and ophthalmic instruments. More particularly, the present invention relates to safety devices for use with laser eye surgery systems.

Photorefractive keratectomy (PRK) and phototherapeutic keratectomy (PTK) employ laser beam delivery systems for directing laser energy to a patient's eye in order selectively to ablate corneal tissue to reform or sculpt the shape of the cornea thereby to improve vision. Present commercial systems employ excimer lasers, where the beams from the lasers are spatially and/or temporally integrated in order to form a beam typically having uniform characteristics. In particular, the beams are often integrated in order to display a flat intensity profile over a circular target region, often referred to as a "top hat" profile.

Such uniformly integrated beams may be used in different ways in order to effect corneal ablation. In a first type of system, positioning of the beam is generally fixed and the beam has a cross-sectional area generally corresponding to an entire surface area of a surgical site on the cornea. Cross-sectional portions of the beam are then sequentially masked or adjusted so as to selectively vary the amount of energy exposure of different portions of the surgical site so as to effect the desired sculpting. This can typically be achieved by using an iris or other exposure control mechanism. While highly effective and relatively easy to control, employing a laser beam having a cross-sectional area generally equal to the area of the treatment or surgical site (typically having a diameter of 5.0 mm to 10.0 mm) often involves the use of relatively large amounts of energy. This is typically relatively expensive, and leads to relatively large laser systems.

As an alternative to such large beam diameter systems, laser "scanning" systems can be employed for corneal ablation. Such scanning systems typically employ a laser beam having a smaller cross-sectional area, thereby decreasing energy requirements. Accordingly, laser scanning systems delivering laser beams of relatively small cross-sectional area can be more economic to use and normally are of smaller construction than laser systems having larger diameter beams. However, the use of such small beams complicates certain aspects of the treatment protocols required to perform the sculpting. For example, to achieve a desired level of volumetric tissue removal or ablation from the eye, the treatment beam is scanned over or otherwise moved across the eye from one position to a next during the surgical procedure. Movement of the beam is typically achieved through motorized scanning mechanisms, devices, or the like. These scanning mechanisms often regulate the position of an optical element, e.g., the angle of a mirrored surface, or the lateral position of an offset imaging lens, or the like, so as to adjust the lateral position of the beam across the treatment site. In a related type of system, the laser beam is scanned over the corneal surface while varying the cross-section of the laser beam. Regardless, to achieve properly controlled laser exposure over the entire treatment site on the eye, the positioning of a scanning laser beam should be controlled accurately. If the beam resides at one position for too long, due to a jam or malfunction of the scanning mechanism, for example, the desired tissue ablation pattern may not be achieved. A jam of the scanning system may jeopardize the success of the surgery and could cause damage to the patient's eye. Since the laser beam itself is not easily visible, malfunction of the scanning mechanism is not readily detectable by an observer.

Accordingly, it would be desirable to provide a device or subsystem for a laser surgery system which verifies the correct positioning or adjustment of the laser beam. Preferably, such a device should be able to be incorporated into a laser surgery system without interfering with the performance of the surgery. It would also be preferred that the device or subsystem be a cost-effective addition to a laser surgery system. It is envisaged that such a device or subsystem can find particular use in scanning laser beam systems. However, it will be appreciated that such a device or subsystem can also be used with large diameter laser beam systems.

SUMMARY OF THE INVENTION

The present invention provides systems, devices, and methods for verifying the scanning motion or adjustment of a laser beam. The present invention can advantageously be used in laser eye surgery where accurate control of the laser beam is crucial so as to ensure patient safety and successful vision correction. According to one aspect of the present invention a scanning laser beam system is provided which verifies that actual scanning of the laser beam across the treatment site on an eye follows a predetermined scanning sequence. Laser beam position feedback information is provided and compared with expected results. Should the feedback information be inconsistent with the expected results, the procedure is typically interrupted to inhibit injury to the patient resulting from, e.g., equipment failure.

Thus, according to one aspect of the present invention, a laser system is provided for sculpting a portion of the eye. The system includes a laser for generating a laser beam arranged to ablate eye tissue. The laser beam is typically used to sculpt the cornea of the eye (but may be applicable to other areas such as the iris, retina, or the like). A laser beam scanning mechanism is provided to scan the laser beam across the treatment area in accordance with a predetermined ablation pattern or scanning sequence. A motion detector or sensor operatively associated with the laser beam is provided at a position downstream of the scanning mechanism to verify the repositioning of the laser beam. Typically, the scanning mechanism verifies the repositioning of the beam by comparing expected energy readings with actual energy readings as the laser beam is moved successively from one lateral position to a next lateral position across the treatment site. Preferably, a beam splitter is used in the system to split the laser beam into a primary beam and a secondary beam. The beam splitter typically directs the primary beam towards the eye so as to ablate eye tissue and directs the secondary beam to the motion detector.

In one embodiment of the present invention, the laser system uses a motion detector having a photosensitive surface and a mask at least partially covering the photosensitive surface. The motion detector is thereby adapted to block or vary the exposure of the photosensitive surface to laser energy so as to register different energy readings as the beam is moved laterally across the surface in response to movement of the primary beam laterally across the treatment site. The mask typically comprises a covering blocking discrete portions of the surface to vary exposure of the surface to the laser beam as the laser beam is moved laterally thereacross from one position to a next position. The mask may have a configuration that blocks varying amounts of energy reaching the sensor as the beam is moved along an arbitrary X-axis of the sensor or an arbitrary Y-axis of the sensor. The position is verified by sequentially comparing expected energy values with the actual energy readings measured by the sensor as the secondary beam moves laterally across the photosensitive surface per the predetermined ablation pattern. Typically, the mask has a configuration that is asymmetric about the X-axis of the sensor, or the Y-axis of the sensor, or both. Preferably, the mask covers about 50% of the photosensitive surface.

According to another aspect of the present invention, a method is provided for verifying the motion of a laser beam across a treatment site on a patient's eye. The method includes directing a laser beam onto a motion detector or sensor. The detector includes a photosensitive surface and a mask which causes the percentage of the photosensitive surface exposed to the beam to vary as the beam is scanned from one position to a next position during a corrective eye surgery scanning procedure. The expected energy values derived from the sensor are sequentially compared with actual energy readings measured by the sensor. If the readings do not correspond with the expected values, the beam may be interrupted or otherwise repositioned to inhibit the laser beam from harming the patient's eye.

A further understanding of the nature and advantages of the invention will become apparent by reference to the remaining portions of the specification and drawings.

BRIEF DESCRIPTION OF THE DRAWINGS

The invention will now be described, by way of example, and with reference to the accompanying drawings, in which.

DESCRIPTION OF THE SPECIFIC EMBODIMENTS

The present invention provides systems, devices, and methods for laser surgery systems, particularly, though not necessarily exclusively, for laser surgery systems of the scanning type. In particular, the present invention provides a system with safety devices arranged to verify laser beam position during the course of corrective surgical sculpting of the eye. By verifying that the actual laser beam has moved to a position corresponding with a predetermined position dictated by a predetermined adjustment sequence or ablation pattern, the system can verify that mechanisms used to scan or move the beam from one position to a next position are functioning properly. This can improve safety of the laser surgery system by enabling the system to detect malfunctions in, e.g., the scanning mechanism, and to interrupt the surgical procedure should actual laser beam position not correspond with a corresponding position dictated by the predetermined adjustment sequence. In this manner, substantial injury to the patients' eye can be inhibited in the case of, e.g., system malfunction.

By "scanning," it is meant that an ablative laser beam is moved successively from one lateral position to a next lateral position across the treatment site on an eye so as to expose successive portions of the eye to a predetermined amount or dosage of laser energy. Usually, the laser system will be operated in a pulsed manner and the exposure at any particular position will result from a number of pulses which occur over a very short time period. The corrective eye procedure is normally completed when the ablative laser beam has completed the scanning sequence in accordance with a predetermined ablation pattern.

Figure 1:
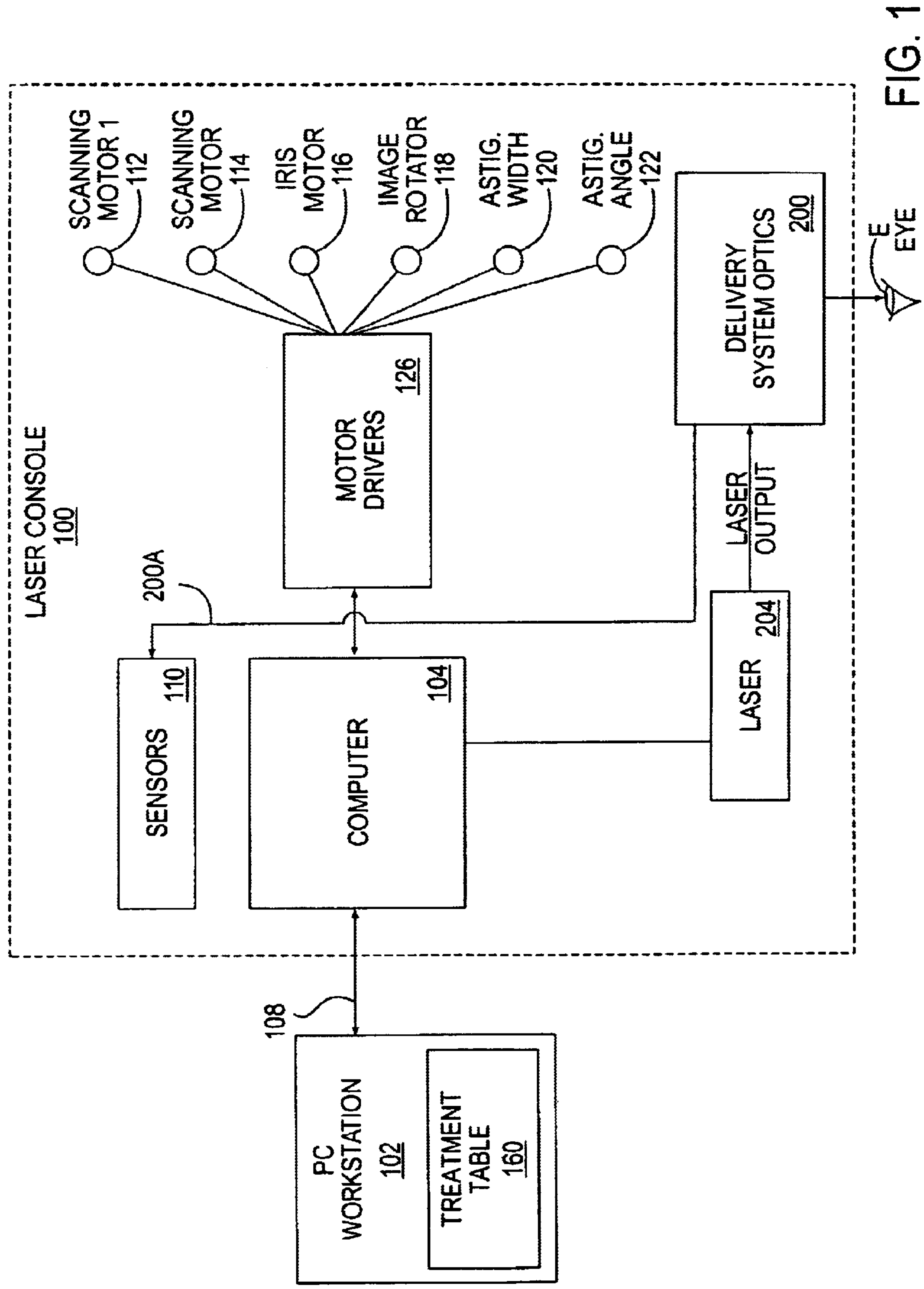
FIG. 1 shows a schematic block diagram indicating a laser surgery system according to the present invention.

Referring to FIG. 1 of the drawings, a block diagram corresponding to a laser eye surgery system in accordance with the invention will now be described in general. The block diagram of FIG. 1 schematically illustrates an ophthalmological surgical control and treatment system 100 which employs a scanning laser. The system 100 typically includes a computer workstation 102 coupled to a computer 104 by means of a bus connection 108. Workstation 102 and the other components of system 100 may comprise the elements of the VISX TWENTY/TWENTY EXCIMER LASER SYSTEM or the VISX STAR Excimer Laser System™, which are available from VISX, Incorporated, of Santa Clara, Calif. or any other appropriate laser refractive surgery systems. Laser surgery system 100 includes a plurality of sensors generally indicated by reference numeral 110 which produce feedback signals from movable mechanical and optical components 200 of ophthalmological laser surgery system 100 as indicated by arrow 200A. The movable mechanical and optical components 200 typically include an iris motor 116, an image rotator 118, astigmatism width motor 120, an astigmatism angle motor 122, and/or the like. Scanning motors 1 (112) and 2 (114) can typically be provided and are typically operatively associated with reflecting or refracting surfaces, e.g., mirrors, offset imaging lenses, or the like, to vary positions of the reflecting surfaces or imaging lenses to effect scanning of the laser beam across a patient's eye.

The feedback signals from the sensors 110 are communicated to the computer 104 via appropriate signal conductors. The computer is typically an STD bus compatible single board computer using a type 8031 microprocessor, although any appropriate computer can be used instead. The computer 104 controls the operation of the motor drivers generally designated with reference numeral 126 for operating the motors 112, 114, 116, 118, 120, and 122. In addition, the computer 104 controls the operation of the laser 204, which is conveniently an ArF laser with a 193 nm wavelength. The laser 204 is arranged typically to provide feedback stabilized fluence of about 160 $mJ/cm^2$ to a cornea of the patient's eye E via the delivery system optics 200. However, other lasers having wavelengths in the ultraviolet range (less than 400 nm), such as between 200–215 nm, solid state lasers, gas lasers, or the like, may be used instead. In FIG. 1, other ancillary components of the laser surgery system 100 which are not necessary for an understanding of the invention, such as a patient eye fixation and/or tracking system, an ablation effluent evacuator/filter, a gas delivery system, and the like, have been omitted for ease of description. Similarly, a keyboard, a display, and other conventional computer subsystem components, such as flexible and hard disk drives, memory boards, and the like, have been omitted.

The laser surgery system 100 may be used for procedures such as photorefractive keratectomy (PRK), phototherapeutic keratectomy (PTK) and Laser in situ keratomileusis (LASIK), for example. Using workstation 102, an operator enters at least one patient treatment parameter, or patient eye specific parameter, corresponding to the desired reshaping or sculpting of the patient's eye, such as, for example, the desired change in patient refraction, or the like. From this information, computer 102 determines a treatment table 160 defining the ablation pattern which includes sequential positions of the reflecting surfaces, in this case, which are used to guide the laser beam to the treatment site on the eye so as to cause the eye sculpting procedure to be performed automatically. In PRK, the laser surgery system 100 is used to ablate underlying tissue of the cornea after removal of the epithelium. The system may be used for initial removal of the epithelium before commencement of reshaping of the underlying tissue. Alternatively, during LASIK procedures, a region or flap of the cornea comprising epithelium, Bowman's membrane and stroma is partially incised and folded back to expose underlying stroma to the laser. Typically, to correct for myopia, for example, using the scanning laser, the laser beam is scanned across the cornea in accordance with a predetermined ablation pattern as defined by the treatment table. For myopia, the ablation or treatment site on the patient's eye typically comprises a circular region having a diameter of between about 0.5 to 7 mm, in which it is desired to reduce the radius of curvature of the cornea to improve vision. The system 100 typically employs a laser beam having a diameter of about 1 to 2 mm which is scanned across the treatment site to correct for myopia, for example.

Figure 2:
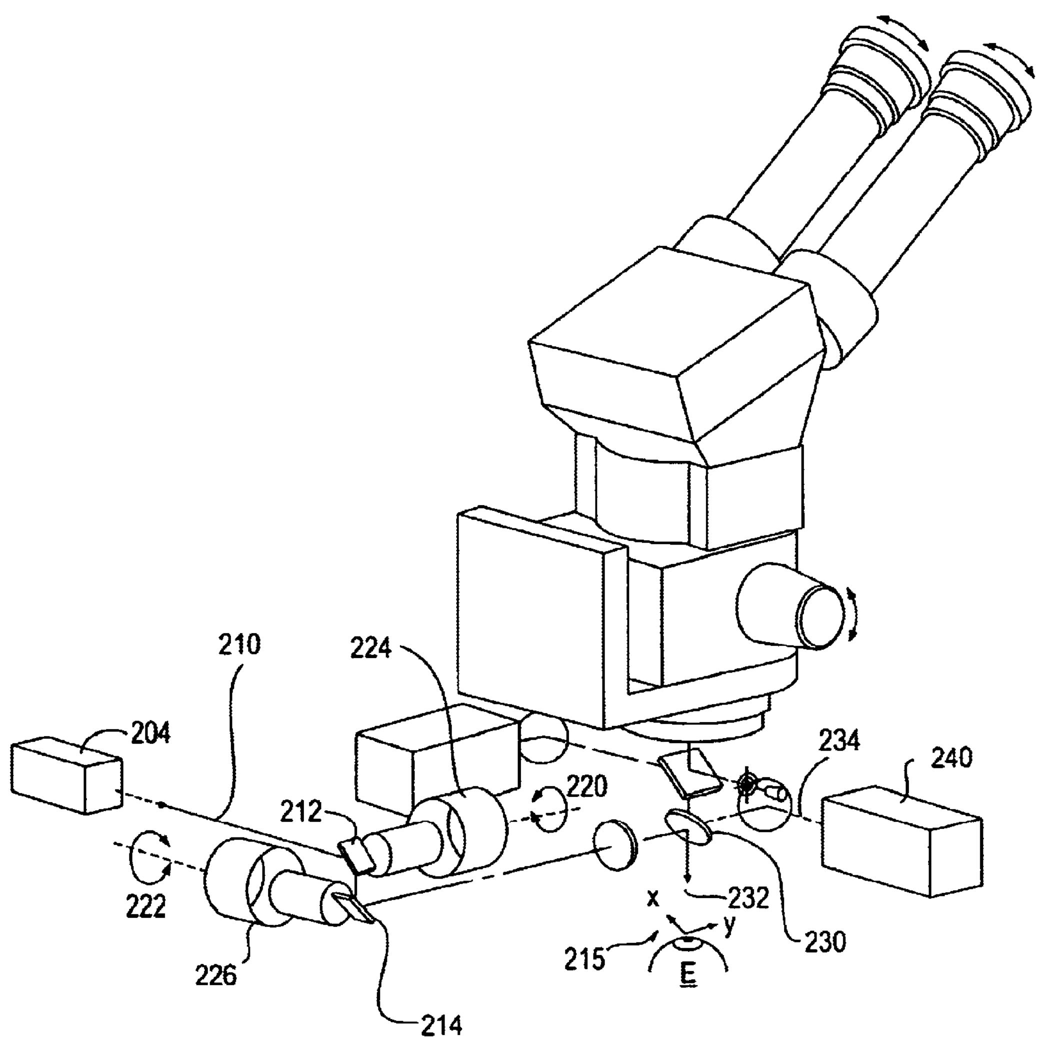
FIG. 2 shows a schematic three-dimensional view of an optical train of the system and indicates a motion detector according to the present invention.

Referring now to FIG. 2 of the drawings in which like reference numerals are used to designate similar parts unless otherwise stated, a portion of an optical train for use in a scanning laser system according to the present invention will now be described in further detail. As previously mentioned, a scanning laser uses a relatively small diameter laser beam, e.g., about 1 to 2 mm in diameter, or the like, which is scanned or otherwise moved across the eye to sculpt the eye in accordance with the desired ablation pattern. As indicated in FIG. 2, the laser 204 directs an ablative laser beam 210 onto a first reflective surface 212 which cooperates with a second reflective surface 214. The reflective surfaces 212, 214 are angularly adjustable, as indicated by arrows 220 and 222, thereby to displace a lateral laser beam position across the treatment area on the patient's eye. The reflecting surfaces 212, 214 are operatively associated with adjustment mechanisms 224, 226, respectively, which are typically in the form of motorized devices such as galvos. The galvos 224, 226 are typically driven by the scanning motors 112, 114, respectfully. It will be appreciated, with reference to FIG. 2 of the drawings, that rotation of the reflecting surface 212 by the galvo 224 varies the position of the laser beam at eye E along an arbitrary X-axis while rotation of reflecting surface 214 varies the position of the laser beam along an arbitrary Y-axis, with reference to an X-Y coordinate reference frame indicated at 215.

The reflected laser beam 210 emanating from the reflecting surfaces 212, 214, is then directed towards the eye through a beam splitter 230 typically in the form of a partially silvered mirror, or prism, or the like. The beam splitter 230 splits the laser beam into a primary beam 232 directed towards the surgical area of the eye E, and a secondary beam 234 directed towards a position verification detector or motion sensor 240. It will be appreciated that splitting the laser beam into the primary and secondary beams in this manner causes the secondary beam to simulate lateral movement of the primary beam. Accordingly, as the primary beam scans across the treatment site on the patient's eye, the secondary beam scans across sensor 240. Advantageously, motion sensor 240 is positioned at generally the same focal distance from mirror 214 as the eye of the patient.

Figure 3:
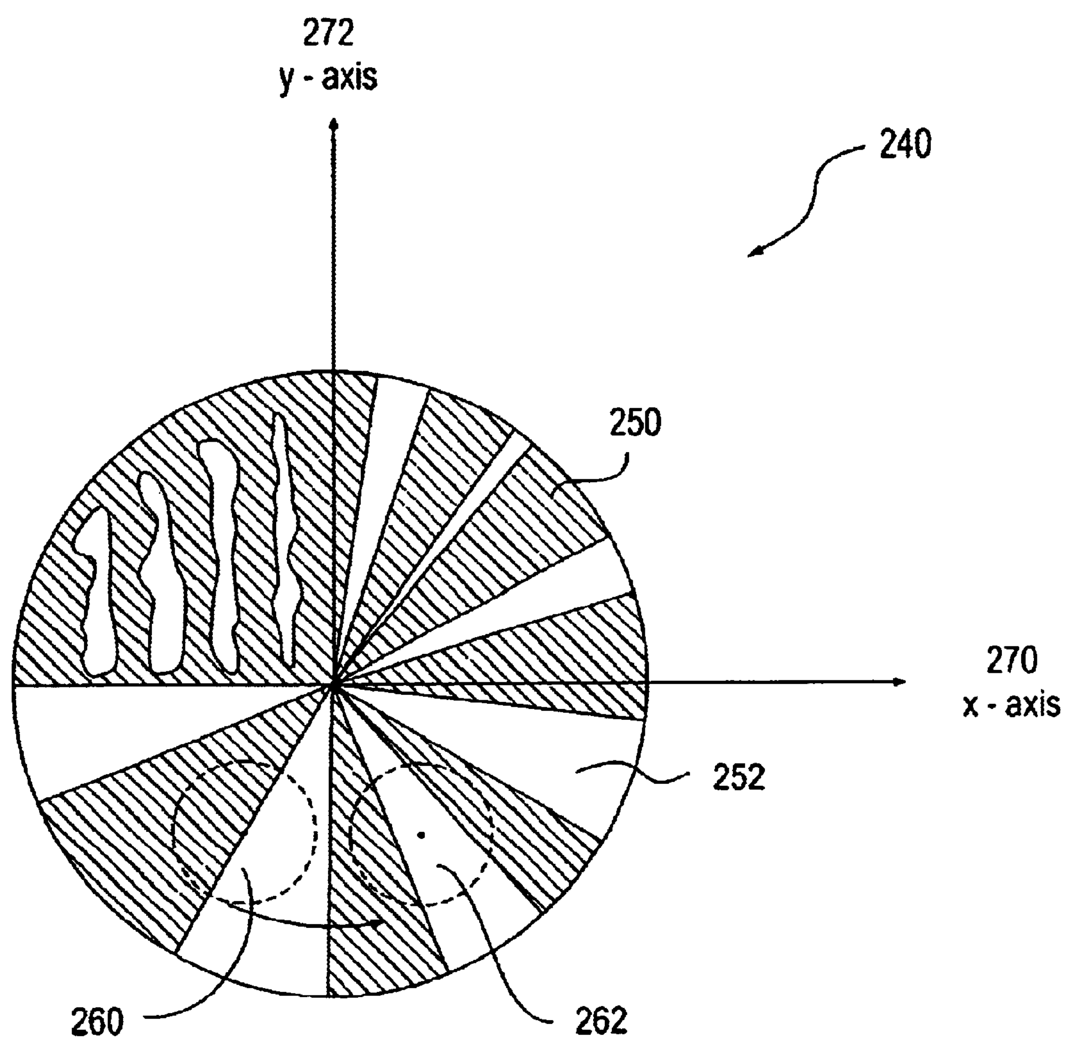
FIG. 3 shows an embodiment of the energy motion sensor, the motion sensor including a photosensitive surface partially covered by a mask, according to the present invention.

Referring now to FIG. 3, one embodiment of motion sensor 240, according to the present invention, will now be described in greater detail. Sensor 240 is used to verify that the beam scanning mechanisms 224 and 226 are functioning properly. Energy sensor 240 has a mask 250, indicated in the shaded regions, which covers an energy or photosensitive surface 252. Mask 250 blocks selected portions, typically totaling about 50%, of energy sensitive surface 252. Sensor 240 is used to verify the positions of the laser beam during the course of the surgical procedure. This is achieved by sequentially measuring energy readings as the laser beam is scanned from one position to a next position in accordance with the predetermined ablation pattern as computed by computer 102. Naturally, since the laser beam's position changes sequentially, the measured energy also varies due to varying portions of the beam being blocked by mask 250. The actual measured values are compared with expected energy values determined by treatment table 160 derived at station 102. The energy values determined by station 102 are readily determined since the sequential positions of the laser beam are determined by the required ablation pattern, and, accordingly, when these positions are compared with where the laser beam should be positioned on sensor 240, a corresponding sequence of expected energy values is determined. Thus, workstation 102 sequentially compares predetermined anticipated energy values with corresponding actual energy readings derived from sensor 240 during the course of the operation. If the actual readings do not correspond with the expected values within acceptable tolerances, then it is assumed that an error has occurred in the system, e.g., in the beam scanning mechanisms or galvos 224 and 226. The surgical procedure is then typically interrupted or the beam is repositioned to inhibit inadvertent injury to the patient's eye.

As seen in FIG. 3, lateral movement of the laser beam from a first position at 260 for example, to a subsequent second position at 262 during the scanning procedure will cause the amount of laser energy exposure of photosensitive surface 252 to vary since differing amounts of the cross-sectional area of the laser beam is masked. In this manner differing energy readings are successively obtained depending on the position of the beam on sensor 240 as its lateral position changes. Preferably, mask 250 has a configuration that is asymmetric about an X-axis 270 or a Y-axis 272 so that movement between different halves and preferably different quadrants will register different energy values. Mask 250 may be a covering having a plurality of asymmetric openings. Mask 250 can be made from any suitable material, such as a hardened polymer, aluminum, or other preferably opaque material, or the like.

Figure 4:
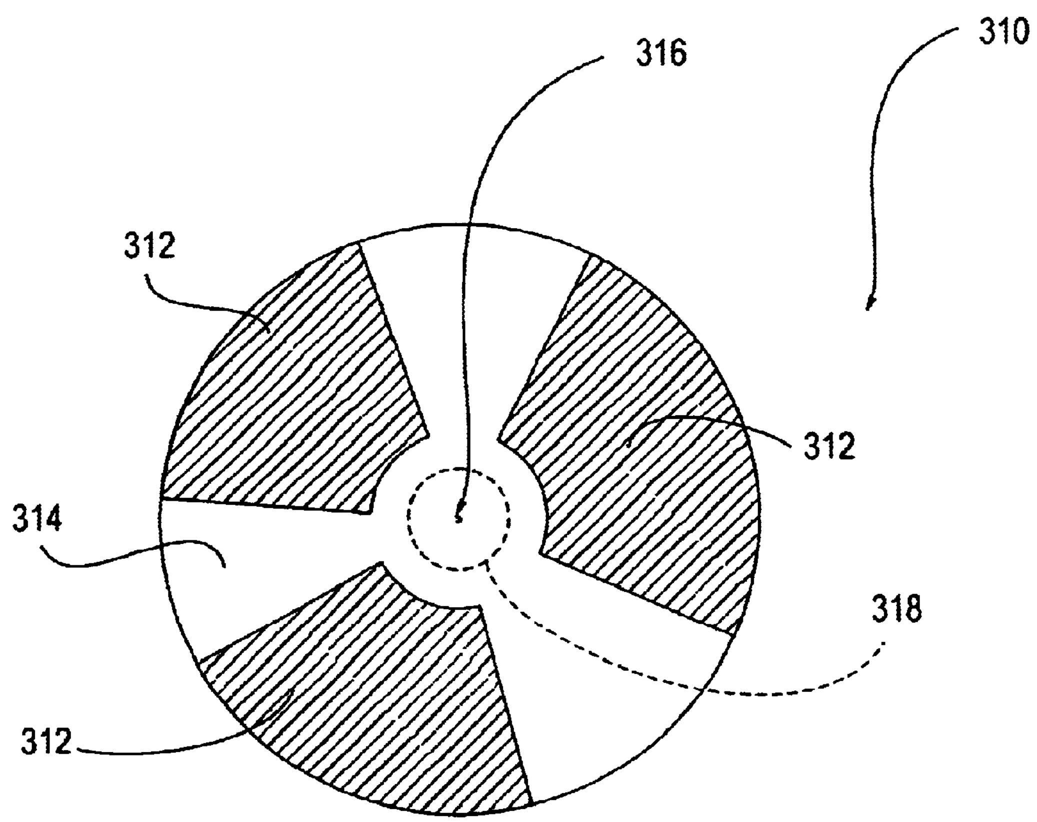
FIG. 4 shows a preferred embodiment of the energy motion sensor.

A preferred embodiment of the mask is indicated by reference numeral 310 in FIG. 4 of the drawings. The shaded regions indicated by reference numerals 312 indicate the mask and the clear region 314 indicates an exposed surface area of an energy sensitive surface of a suitable photosensitive device, e.g., a 10 mm pyrodetector, or the like. Naturally, the masked regions 312 will cause actual energy readings to vary from one lateral beam position to the next as the cross-sectional area of the beam is successively blocked in varying amounts as the lateral beam position is varied thereby causing varying exposure of the photosensitive surface to the beam. Accordingly, mask 310 functions in similar fashion to mask 250.

The mask 310 includes a central portion or region 316. Advantageously, the central region 316 can be used to calibrate the fluence of the laser beam. This is typically achieved by closing a patient shutter (not shown) positioned in front of the patient's eye so that the primary laser beam does not ablate patient eye tissue during calibration. An aperture wheel, (not shown) typically positioned at laser 204, is then typically set to a specific cross-sectional size, e.g., 2 mm, or the like. The laser beam is then directed so as to cause the secondary beam to be centered on region 316. It will be appreciated that the entire cross-sectional area of the beam then impinges on the exposed surface of sensor 310 at central region 316, as indicated in dashed lines by reference numeral 318. A predetermined number of laser beam shots, typically 150 shots, or the like, are then fired on sensor 310. Typically, an initial number of shots, 50 for example, is disregarded to take into account stabilizing factors, such as warming up of laser 204, for example. An average measurement of the fluence for the following 100 shots is then determined. This average value is then compared with a fluence value desired for the surgical operation. If these values do not correspond, laser 204 can then be adjusted so as to vary the fluence of the laser. A further 100 shots of the adjusted laser beam is then fired at sensor 310. The average fluence for these 100 shots is then again determined and compared with the fluence desired for the procedure. This process is repeated until the average fluence reading corresponds with the fluence which is desired for the operation.

Once the desired fluence has been achieved in this manner, the patient's shutter is opened and the surgical procedure can be performed as described above.

It will be appreciated that when the fluence of the laser has been achieved in this manner, the expected energy readings corresponding to the ablation pattern are determined by using this fluence value. Accordingly, as the surgical procedure progresses in accordance with the ablation pattern, the actual energy readings derived from sensor 310 are compared with expected values, both the expected and the actual values corresponding with a specific fluence value.

While the above is a complete description of the preferred embodiments of the invention, various alternatives, modifications, and equivalents may be used. For example, in alternative embodiments, the energy sensor 240 may comprise a quadrant sensor. A quadrant sensor uses a separate sensor for each of the four quadrants shown in FIG. 3. The amount of energy registered by any one, or more, quadrants is used to determine the location of the laser beam. Of course, additional sensors may be used to divide the circle into further subsections (eighths, sixteenths, etc). However, additional sensors also increase overall cost. A CCD sensor may also be used in place of sensor 240 with a mask or a quadrant sensor. A CCD sensor, however, also introduces additional cost. In further alternatives, it may be possible to use various translucent materials as a mask to vary the amount of energy passing through the mask. The above description, though complete, should not be taken as limiting the scope of the invention which is defined by the appended claims.

What is claimed is:

1. A corrective eye surgery system including:

a laser for generating an ablative laser beam arranged to ablate eye tissue;

a computer programmed to effect a desired position adjustment sequence for sequentially adjusting the ablative laser beam, the desired position adjustment sequence including a desired lateral position having a first central axis and a subsequent desired lateral position having a second central axis across a treatment area on a patient's eye, the second axis being non-concentric with the first axis;

a laser beam adjustment mechanism for adjusting the position of the laser beam in accordance with the desired position adjustment sequence so as to ablate successive portions of the patient's eye extending across the treatment area on the eye during an ablation procedure; and a comparing system for comparing actual positions of the laser beam to desired positions at at least the desired lateral position having the first central axis and the subsequent desired lateral position having the second central axis as the ablation procedure progresses with the desired position adjustment sequence.

2. A system as claimed in claim 1, wherein the computer is programmed to determine the desired adjustment sequence upon entry of a patient eye specific parameter into the computer.

3. A system as claimed in claim 1, which further includes a sensor positioned across a path of the laser beam, the sensor monitoring the positions of the laser beam.

4. A system as claimed in claim 3, which further includes a beam splitter, the laser beam being a source beam, the splitter splitting the source beam into a primary beam directed at the treatment area to perform the ablation procedure and a secondary beam directed at the sensor.

5. A system as claimed in claim 4, wherein the sensor includes a laser energy sensitive surface configured to yield different energy values depending upon the position of incidence of the secondary laser beam thereon.

6. A system as claimed in claim 5, wherein the computer is programed to calculate expected energy values of the sensor corresponding to at least some laser beam positions determined by the adjustment sequence and in which the sensor is operatively connected to the computer to enable the computer to compare actual energy values from the sensor with the expected energy values, so as to compare actual laser beam adjustment with the desired adjustment sequence.

7. A system as claimed in claim 5, wherein the laser energy sensitive surface includes an underlying energy sensitive surface and a mask covering portions of the underlying surface so that as the position of incidence of the laser beam changes across the energy sensitive surface, a different portion of the beam is blocked by the mask thereby changing the degree of exposure of the underlying surface to the beam and consequently varying the energy value.

8. A system as claimed in claim 5, wherein the sensor is a quadrant sensor.

9. A system as claimed in claim 5, wherein the sensor is a CCD sensor.

10. A laser system for sculpting a portion of the eye, said system comprising:

a laser for generating a laser beam suitable for ablation of said portion of the eye;

a laser beam adjustment mechanism optically coupled to said laser beam for laterally deflecting said laser beam to create an ablation pattern including a lateral position and a subsequent non-concentric lateral position on said eye; and an energy motion sensor optically coupled to at least a portion of said laser beam downstream from said laser beam adjustment mechanism for confirming deflection of the laser beam by said adjustment mechanism at at least the lateral position and the subsequent non-concentric lateral position; and a mask disposed between said beam and said sensor, said mask having a configuration adapted to vary exposure of the sensor to the laser beam as the beam moves laterally across the sensor through the series of positions.

11. A laser system as in claim 10, wherein said laser beam adjustment mechanism comprises at least one galvanometer optically coupled to said laser beam, said galvanometer having a reflective surface for repositioning said laser beam to alter the ablation pattern on the eye.

12. A laser system as in claim 10, wherein said mask comprises a plurality of openings adapted to vary exposure of the sensor to the beam;

said beam being of sufficient size to create distinct energy readings for each position of the beam on the sensor.

13. A laser system as in claim 10, wherein said configuration limits the amount of energy from the beam reaching the sensor as the beam is moved along an X-axis of the sensor.

14. A laser system as in claim 10, wherein said configuration limits the amount of energy from the beam reaching the sensor as the beam is moved along a Y-axis of the sensor.

15. A laser system as in claim 10, wherein said configuration is asymmetric about an X-axis of the sensor.

16. A laser system as in claim 10, wherein said configuration is asymmetric about a Y-axis of the sensor.

17. A laser system as in claim 10, wherein said energy motion sensor further comprises a mask having a plurality of openings to partially block said laser beam on the sensor to create a plurality of locations on the sensor adapted to produce distinct energy readings.

18. A laser system as in claim 10, further comprising a beam splitter separating the laser beam into a primary beam and a secondary beam, said beam splitter directing said primary beam towards the eye.

19. A laser system as in claim 10, wherein the sensor comprises a quadrant sensor.

20. A laser system as in claim 10, wherein the sensor comprises a CCD sensor.

21. A method for verifying motion of a laser beam comprising:

transmitting a laser beam onto a position on an energy sensor having a mask that controls a percentage of the energy sensor exposed to the beam at each position on the sensor;

determining an expected energy reading based on the percentage of the energy sensor exposed to the beam at the position on the energy sensor; and comparing the expected energy reading of the sensor with an actual energy reading for said position on the sensor.

22. A method as in claim 21, further comprising turning off said laser beam if said actual energy reading does not match said expected energy reading.

23. A method as in claim 21, wherein the transmitting of the laser beam comprises splitting said laser beam into a primary beam and a secondary beam and transmitting said secondary beam onto the energy sensor and directing said primary beam towards a target surface.

24. A method of performing corrective eye surgery, the method, including:

determining a desired position adjustment sequence for sequentially adjusting the position of an ablative laser beam, the desired position adjustment sequence including a desired lateral position and a subsequent non-concentric desired lateral position across a treatment area on a patient's eye;

adjusting the laser beam in accordance with the desired position adjustment sequence by laterally deflecting the beam between actual positions so as to ablate successive portions of the patient's eye extending across the treatment area on the eye during an ablation procedure; and comparing actual positions of the laser beam to desired positions at at least the desired lateral position and the subsequent non-concentric desired lateral position as the ablation procedure progresses with the desired position adjustment sequence.

25. A method as claimed in claim 24, which further includes interrupting the ablation procedure should the actual adjustment of the laser beam deviate from the desired adjustment sequence.

26. A method as claimed in claim 24, wherein the determining step includes entering a patient specific parameter into a computer and causing the computer to determine the desired adjustment sequence.

27. A method as claimed in claim 26, wherein an adjustment mechanism is operatively linked to the computer, the method including transmitting instructions from the computer to the adjustment mechanism to cause the adjustment mechanism to scan the laser beam across the treatment area in accordance with the desired adjustment sequence.

28. A method as claimed in claim 24, wherein the laser beam is a source laser beam and the comparing step includes splitting the source laser beam into a primary beam directed onto the treatment area to perform the ablation procedure and a secondary beam directed at a sensor arranged to monitor actual adjustment of the source laser beam.

29. A method as claimed in claim 28, wherein the sensor has a laser energy sensitive surface, the comparing step further including simulating adjustment of the primary beam across the treatment area by the secondary beam on the laser energy sensitive surface of the sensor.

30. A method of performing corrective eye surgery, the method including:

determining a desired position adjustment sequence for sequentially adjusting the position of an ablative laser beam, the desired position adjustment sequence including a desired lateral position and a subsequent non-concentric desired lateral position across a treatment area on a patient's eye;

adjusting the laser beam in accordance with the desired position adjustment sequence by laterally deflecting the beam between actual positions so as to ablate successive portions of the patient's eye extending across the treatment area on the eye during an ablation procedure;

comparing actual positions of the laser beam to desired positions at at least the desired lateral position and the subsequent non-concentric desired lateral position as the ablation procedure progresses with the desired position adjustment sequence, wherein the laser beam is a source laser beam and the comparing step includes splitting the source laser beam into a primary beam directed onto the treatment area to perform the ablation procedure and a secondary beam directed at a sensor arranged to monitor actual adjustment of the source laser beam, and wherein the sensor has a laser energy sensitive surface, the comparing step further including simulating adjustment of the primary beam across the treatment area by the secondary beam on the laser energy sensitive surface of the sensor; and selectively masking the laser energy sensitive surface so as to yield differing energy values depending on a position of incidence of the secondary beam thereon.

31. A method as in claim 30, wherein the laser beam comprises a series of discrete pulses and wherein a laser beam adjustment mechanism repositions said laser beam between pulses.

32. A method as claimed in claim 30, which includes progressively comparing successive energy values actually derived from the sensor with energy values associated with the desired adjustment sequence so as to compare actual adjustment of the laser beam with the desired adjustment sequence.

* * * * *